(12) United States Patent
Okuda (10) Patent No.: US 8,075,543 B2
(45) Date of Patent: Dec. 13, 2011

(54) DISPOSABLE DIAPER AND PROCESS OF PRODUCING THE SAME

(75) Inventor: Yasuyuki Okuda, Tochigi (JP)

(73) Assignee: Kao Corporation, Tokyo (JP)

( * ) Notice: Subject to any disclaimer, the term of this patent is extended or adjusted under 35 U.S.C. 154(b) by 776 days.

(21) Appl. No.: 11/988,666

(22) PCT Filed: Apr. 28, 2006

(86) PCT No.: PCT/JP2006/308983
§ 371 (c)(1),
(2), (4) Date: Mar. 26, 2008

(87) PCT Pub. No.: WO2007/007457
PCT Pub. Date: Jan. 18, 2007

(65) Prior Publication Data
US 2008/0312631 A1    Dec. 18, 2008

(30) Foreign Application Priority Data
Jul. 12, 2005  (JP) .................................. 2005-203696

(51) Int. Cl.
*A61F 13/20* (2006.01)
(52) U.S. Cl. .................... 604/385.28; 604/365; 604/381; 604/378; 604/366; 156/164; 156/566; 156/301; 156/292; 156/291; 156/298; 156/299; 156/300; 156/324
(58) Field of Classification Search .................. 604/378, 604/366, 385
See application file for complete search history.

(56) References Cited

U.S. PATENT DOCUMENTS

| | | | |
|---|---|---|---|
| 3,860,003 A * | 1/1975 | Buell | 604/385.25 |
| 4,934,535 A | 6/1990 | Muckenfuhs et al. | |
| 5,013,382 A * | 5/1991 | Nalowaniec et al. | 156/298 |
| 5,370,634 A * | 12/1994 | Ando et al. | 604/385.21 |
| 6,132,410 A | 10/2000 | Van Gompel et al. | |
| 6,156,024 A * | 12/2000 | Schulte et al. | 604/385.28 |
| 6,682,515 B1 | 1/2004 | Mizutani et al. | |

(Continued)

FOREIGN PATENT DOCUMENTS

JP      6-1374 A      1/1994

(Continued)

OTHER PUBLICATIONS

Extended European Search Report for Application No. 06745842.2 dated Dec. 8, 2010.

(Continued)

*Primary Examiner* — Tatyana Zalukaeva
*Assistant Examiner* — Ilya Treyger
(74) *Attorney, Agent, or Firm* — Birch, Stewart, Kolasch & Birch, LLP (57) ABSTRACT

A disposable diaper 1 includes a topsheet 2, a backsheet 3, and an absorbent member 4 between the sheets 2 and 3. A pair of leg flaps 5 each having an elastic member is provided along the laterally opposite side edges of the absorbent member 4. Each of the leg flaps 5 is fixed at its front end portion 52 and rear end portion 53 to a portion C, one of longitudinally opposite end portions of the diaper, and to a portion B, the other end portion, in such a configuration that each of the leg flaps 5 may be folded back over the side of the backsheet 3 when the disposable diaper 1 is in a flat-out state with the elastic members stretched.

10 Claims, 4 Drawing Sheets

U.S. PATENT DOCUMENTS

2003/0004488 A1 1/2003 Ashton et al.
2008/0167634 A1* 7/2008 Kouta et al. .................. 604/367

FOREIGN PATENT DOCUMENTS

| | | |
|---|---|---|
| JP | 6-75445 U | 10/1994 |
| JP | 2000-254175 A | 9/2000 |
| JP | 2001-293029 A | 10/2001 |
| JP | 2001-520082 A | 10/2001 |
| JP | 2001-309938 A | 11/2001 |
| JP | 2002-177324 A | 6/2002 |
| JP | 2002-522177 A | 7/2002 |
| JP | 2003-290278 A | 10/2003 |
| JP | 2006-43326 A | 2/2006 |
| WO | WO-99/20215 A1 | 4/1999 |
| WO | WO-00/09199 A1 | 2/2000 |
| WO | WO 2004/105664 A1 | 12/2004 |

OTHER PUBLICATIONS

Japanese Office Action for Application No. 2005-203696 dated Dec. 7, 2010.

* cited by examiner

DISPOSABLE DIAPER AND PROCESS OF PRODUCING THE SAME

TECHNICAL FIELD

The present invention relates to a disposable diaper, particularly a disposable diaper with leg flaps.

BACKGROUND ART

Disposable diapers provided with leg flaps are widely known. Diapers of this type have a pair of leg flaps along laterally opposing sides (longer sides) thereof.

In putting a disposable diaper of this type on a child, the leg flap may be tucked inside around the legs. If the leg flap is left as tucked in, the diaper can leak along the leg flap while worm. Then, it is necessary for a caregiver to check around the leg openings to be sure that the diaper is not tucked in after each diaper change, which is troublesome.

A disposable diaper having leg flaps folded back laterally outward is known.

For example, JP 2001-309938A (hereinafter "document 1") discloses a disposable diaper having a pair of leg flaps, in which each leg flap has three elastic members disposed to extend in the longitudinal direction of the flap in a laterally middle portion of the flap, and the leg flap is folded back laterally outward along a folding line positioned outboard of the most inboard edge of the most inboard one of the three elastic members.

JP 2001-293029A (document 2) discloses a method of packaging a disposable diaper, in which a diaper is longitudinally folded in three with each leg flap folded laterally outward.

JP 2001-520082A (document 3) and JP 2002-522117A (document 4) disclose a disposable diaper, in which the most outboard leg elastic member is disposed near the distal edge of the leg flap, and a separately provided sheet is joined on the upper side (skin facing side) of the leg elastic members. Since the leg elastic member is disposed near the distal edge of the leg flap, the distal part of the leg flap forms substantially no frill. Therefore, the leg flap is prevented from being tucked inside when the diaper is put on a child. This makes a diaper change smooth because there is no need for a caregiver to give attention to the leg openings.

Either of the diapers of documents 1 and 2 has no means for fixing the outward fold of the leg flaps although a folding crease is formed on folding the leg flaps outward. Either diaper has no effect in directing the leg flaps outward while worn so that the leg flaps may be tucked into the inside of the leg openings when put on.

The diapers of documents 3 and 4 tend to allow the leg gathers to move into the wearer's groins in the crotch portion and toward the cleft of the wearer's buttocks in the buttock portion, which reduces the fit and causes leakage.

DISCLOSURE OF THE INVENTION

The present invention provides a disposable diaper including a topsheet, a backsheet, an absorbent member between the two sheets, and a pair of leg flaps along the laterally opposite side edges of the absorbent member. The leg flaps are elasticized with elastic members. Each of the leg flaps is fixed at a front and a rear end thereof to longitudinally opposite end portions of the diaper, respectively, in such a configuration that the leg flap may be folded back over the backsheet side when the disposable diaper is in a flat-out state with the elastic member stretched.

The present invention also provides a preferred process for producing the disposable diaper. The process includes the step of making a continuous body of the absorbent body including a continuous body of the topsheet, a continuous body of the backsheet, a plurality of absorbent members disposed between the topsheet and the backsheet, and a pair of continuous body of the leg flaps having an elastic member. The pair of continuous body of the leg flaps are disposed along the opposing side edges of the plurality of absorbent members. The process further includes the steps of folding each of the continuous body of the leg flaps over the backsheet side along a position inboard of the elastic member, joining the folded-over portion of each of the continuous body of the leg flaps to the backsheet at predetermined intervals, separately preparing a continuous body of the exterior sheet by cutting a continuous sheet of fiber to make concave shapes on both edges at a prescribed interval symmetrically about the longitudinal centerline, joining the continuous body of the absorbent body to the continuous body of the exterior sheet in alignment such that each pair of leg flaps of the continuous body of the absorbent body may stick out laterally from the edge of the concave shapes of the continuous body of the exterior sheet, and cutting the continuous body of the exterior sheet between adjacent individual absorbent bodies into individual disposable diapers.

The present invention also provides another preferred process of producing the disposable diaper. The process includes the step of making a continuous body of the absorbent body including a continuous body of the topsheet, a continuous body of the backsheet, a plurality of absorbent members disposed between the topsheet and the backsheet, and a pair of continuous body of the leg flaps having an elastic member. The pair of continuous body of the leg flaps are disposed along the opposing side edges of the plurality of absorbent members. The process further includes the steps of folding each of the continuous body of the leg flaps over the backsheet side along a position inboard of the elastic member, joining the folded-back portion of each of the continuous body of the leg flaps to the backsheet at predetermined intervals, separately preparing a plurality of continuous body of the exterior sheets by cutting a continuous sheet of fiber, joining each of the continuous body of the exterior sheet to the continuous body of the absorbent body to straddle two adjacent individual absorbent bodies, and cutting each continuous body of the exterior sheet between the adjacent individual absorbent bodies into individual disposable diapers.

DETAILED DESCRIPTION OF THE INVENTION

A first preferred embodiment of the disposable diaper according to the present invention will be described with reference to FIGS. 1 through 4.

Figure 1:
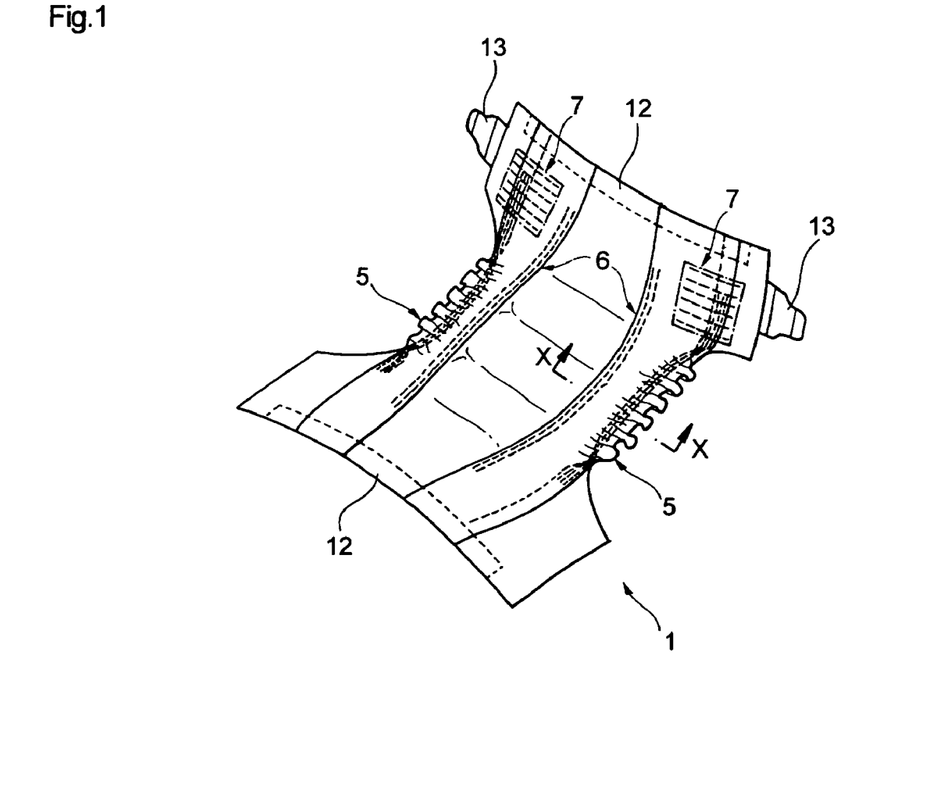
FIG. 1 is a perspective of a disposable diaper incorporating a first embodiment of the invention in its relaxed state.
Figure 2:
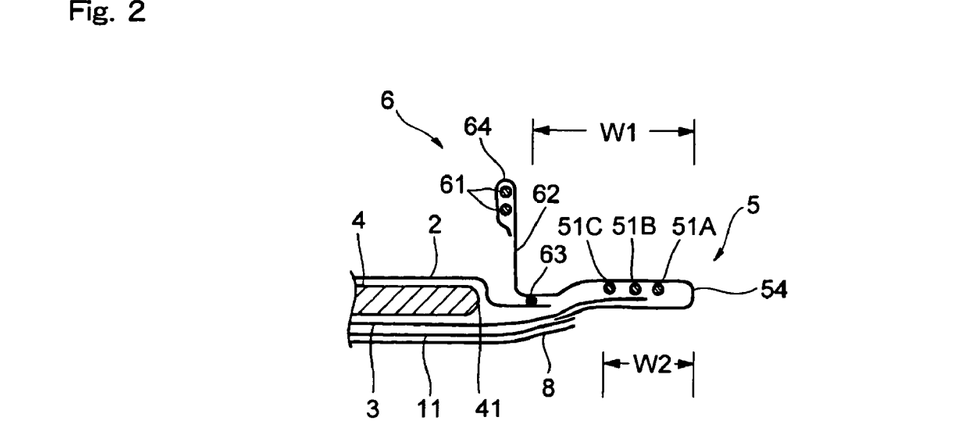
FIG. 2 is an enlarged schematic cross-section of the diaper of the first embodiment, taken along line I-I.
Figure 3:
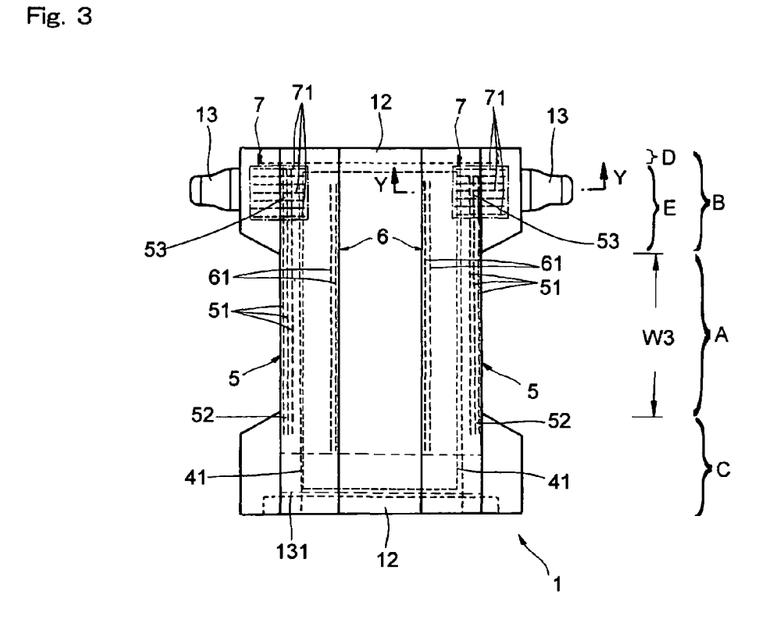
FIG. 3 is a plan of the diaper of the first embodiment in its flat-out state.

The disposable diaper 1 of the first embodiment is a flat type designed for use by a child. As illustrated in FIGS. 1 through 4, the diaper 1 includes a liquid permeable topsheet 2, a liquid impermeable or water repellent backsheet (leak-preventive sheet) 3, and a liquid retentive absorbent member 4 interposed between the topsheet 2 and the backsheet 3. The diaper 1 is provided with a pair of leg flaps 5 along its opposing lateral sides, each leg flap 5 having elastic members 51A, 51B, and 51C. As illustrated in FIGS. 1 and 3, the diaper 1 is also provided with a pair of elasticized, standing cuffs 6 along the lateral sides of the absorbent member 4, each cuff 6 having elastic members 61. The topsheet 2, the backsheet 3, the absorbent member 4, and the pair of leg flaps 5 are assembled to make up an absorbent body 16.

Figure 4:
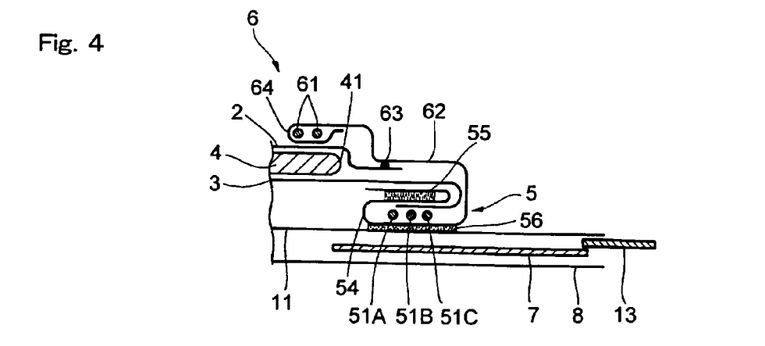
FIG. 4 is an enlarged schematic cross-section of the diaper of the first embodiment illustrated in FIG. 3, taken along line II-II.

As illustrated in FIG. 4, each of the leg flaps 5 is fixed at its front and rear end portions 52 and 53 to a stomach portion C (one of longitudinal end portions of the diaper 1) and a back portion B (the other longitudinal end portion), respectively, in a configuration such that the whole length of the laterally distal portion of the leg flap 5 where the elastic members 51A, 51B, and 51C are provided may be folded back over the side of the leak-preventive sheet 3 when the disposable diaper 1 of the first embodiment is in a flat-out state with the elastic members 51A, 51B, and 51C stretched.

As illustrated in FIG. 3, the disposable diaper 1 of the first embodiment has a crotch portion A in its longitudinally middle portion, a stomach portion C (one of longitudinal end portions) adjacent to and forward of the crotch portion A, and a back portion B (the other longitudinal end portion) adjacent to and rearward of the crotch portion A. The back portion B has a pair of fastening tapes 13 on both side edges thereof, and the stomach portion C has on its outer surface a landing zone 131 where the fastening tapes 13 are to be secured. The crotch portion A is applied to the crotch of a wearer while worn.

The pair of leg flaps 5 used in the disposable diaper 1 of the first embodiment will be described in more detail. Each leg flap 5 forms a leg gather in its outboard side portion. As illustrated in FIG. 2, a water repellent sheet 62 (which forms the elasticized standing cuff 6) extends laterally outwardly from a fixed end 63 and joined to the leak-preventive sheet 3 to form the leg flap 6. As illustrated in FIG. 2, the fixed end 63 is formed by bonding the sheet 62 to the topsheet 2 in a straight line configuration extending in the diaper's longitudinal direction between the side edge 41 of the absorbent member 4 and the leg flap 5. The leg flap 5 and the cuff 6 are fixed to the topsheet 2 along the fixed end 63. While FIG. 2 shows only the right hand side of FIG. 1, the left hand side has quite the same structure. The same applies to FIG. 4.

The laterally distal portion of the sheet 62 making up the let flap 5 is folded back to embrace three elastic members 51A, 51B, and 51C for leg gather formation and the leak-preventive sheet 3 in the fold. The leading edge of the folded-back portion is bonded to the leak-preventive sheet 3 by a known bonding means such as heat sealing or an adhesive.

Each of the elastic members 51A, 51B, and 51C that are disposed in the laterally middle region of each leg flap 5 is an elastic thread and substantially parallel to the free edge 54 of the flap 5 as illustrated in FIG. 3. The sheet 62 is formed into a bag shape outboard of the most laterally outboard elastic member 51A in the flap 5 and gathered to make a frill as illustrated in FIGS. 1 and 2. The elastic members 51A, 51B, and 51C are bonded to the sheet 62 by a known bonding means such as an adhesive.

The leg flap 5 is fixed to a cover sheet 11 at one longitudinal end portion thereof (fixed portion 53) in the back portion B and at the other longitudinal end portion (fixed portion 52) in the stomach portion C.

When the diaper is in a relaxed state, the leg flap 5 in the crotch portion A rises from its fixed end 63 obliquely outwardly, then curves laterally outwardly inboard of the most inboard elastic member 51C, and further extends from the elastic member 51C almost horizontally as illustrated in FIG. 2. In applying the diaper to a child, the leg flap 5 is brought into contact with the leg while being kept open laterally outward as illustrated in FIG. 2. The term "crotch portion" as used herein denotes the portion of the diaper concave on both sides thereof when the diaper is in a flat-out state.

As illustrated in FIG. 2, the leak-preventive sheet 3 extends laterally outward from the lateral side edge 41 of the absorbent member into the leg flap 5 to be sandwiched between the sheet 62 and the elastic members 51B and 51C and joined to the sheet 62. The leak-preventive sheet 3 does not extend beyond the most outboard elastic member 51A of the leg flap 5. An exterior sheet 8 is joined to the leak-preventive sheet 3 via the cover sheet 11.

As illustrated in FIG. 2, the leak-preventive sheet 3 is joined on its upper side to the absorbent member 4, the topsheet 2, and the sheet 62.

The longitudinal end portion of the leg flap 5 in the back portion B (hereinafter referred to as a rear end portion) is folded back over the side of the leak preventive sheet 3 about a position inboard of the most inboard elastic member 51C and fixed as illustrated in FIG. 4 to provide a fixed portion 53. Similarly, the other longitudinal end portion of the leg flap 5 in the stomach portion C (hereinafter referred to as a front end portion) is folded back and fixed to the cover sheet 11 to provide a fixed portion 52.

The disposable diaper 1 of the first embodiment has the exterior sheet 8 under the leak-preventive sheet 3. The fixed portions 52 and 53 of the front and the rear end portions of each leg flap 5 are covered with the exterior sheet 8.

According to the first embodiment, each leg flap 5 is joined in its rear fixed portion 53 to a laterally extensible portion 7 via the cover sheet 11 as illustrated in FIG. 4. While, in the present embodiment, the rear end portion of the leg flap 5 folded over the leak-preventive sheet 3 overlaps the laterally extensible portion 7, the rear end portion of the leg flap 5 may be fixed in a crossing relation with the laterally extensible portion 7. The manner of fixing in the front fixed portion 52 is the same as in the rear fixed portion 53, except that there is no laterally extensible portion 7 provided. Fixing or bonding between any two of the above-described members is done by a known joining means such as heat sealing or an adhesive. While the structure of the front and rear fixed portions 52 and 53 of the leg flap 5 has been described by referring to the flat-out state diaper, this applies whether the diaper is in its flat-out or relaxed state.

In the rear fixed portion 53, the sheet 62 forming the leg flap 5 is joined to itself via a first joint 55 and also joined to the cover sheet 11 via a second joint 56. The first joint 55 and the second joint 56 have almost the same length. The front end of each of the first joint 55 and the second joint 56 is located near the front end of each side of the back portion B of the diaper 1. The rear end of each of the first joint 55 and the second joint 56 is located near the edge of a waist portion D.

It is preferred that the exterior sheet 8 extend forward from the front end of the first joint 55 and cover the garment facing side of the first joint 55 so that the first joint 55 may not be exposed on the garment facing side and scratch the wearer's skin or the first joint 55 may not be debonded by any outer force. The forward extension of the exterior sheet 8 from the front end of the first joint 55 in the longitudinal direction is preferably 3 to 30 mm long. The forward extension of the exterior sheet 8 from the front end of the first joint 55 forms the front end portion of each laterally opposing side portions of the back portion B. The skin facing side of the forward extension is not joined to any other member.

It is preferred that the exterior sheet 8 extent forward from the front end of the second joint 56 and cover the garment facing side of the second joint 56 to obtain the following advantages. Firstly, the kink generated by the leg flap 5 turning to face the skin when the diaper is put on is prevented by the exterior sheet 8 from directly irritating the wearer's skin. Secondly, the leg flap 5 is helped to turn to face the skin during wear. The forward extension of the exterior sheet 8 from the front end of the second joint 56 is preferably 3 to 30 mm in the longitudinal direction. The forward extension of the exterior sheet 8 from the front end of the second joint 56 forms the front end portion of each of the side portions of the back portion B. The skin facing side of the forward extension is not joined to any other member.

While the first and second joints 55 and 56 have been described as for the rear fixed portions 53, the same applies to the front fixed portions 52.

In the first embodiment, the width W1 of the leg flap 5 is preferably constant over its whole length as measured between the fixed end 63 and the free edge 54 in a direction perpendicular to the longitudinal direction along the surface of the leg flap 5 in its flat-out state. Specifically, the width W1 is preferably 10 to 70 mm, more preferably 20 to 50 mm.

The width W2 between the inboard edge of the elastic member 51C and the free edge 54 measured in a direction perpendicular to the longitudinal direction along the surface of the leg flap 5 in its flat-out state is preferably constant over the whole length of the leg flap 5. Specifically, the width W2 is preferably 5 to 50 mm, more preferably 10 to 35 mm.

The length W3 of the leg flap 5 in the crotch portion A in its flat-out state is preferably 50 to 400 mm, more preferably 100 to 300 mm.

The disposable diaper 1 of the first embodiment takes on, in its relaxed state, a cup shape with its skin facing side inside by contractive force of the pair of leg flaps 5 and the pair of standing cuff 6 as illustrated in FIG. 1. In a flat-out state, the disposable diaper 1 has a sandglass shape, i.e., with its longitudinally middle portion narrowed. As used herein, the expression "in a relaxed state" means a state in which no substantial external force other than gravity is exerted on the disposable diaper 1.

As illustrated in FIG. 4, the disposable diaper 1 of the first embodiment has the cover sheet 11 and the exterior sheet 8 underneath the leak-preventive sheet 3. Both the cover sheet 11 and the exterior sheet 8 extend laterally outward from both laterally opposing side edges of the topsheet 2. Both the cover sheet 11 and the exterior sheet 8 have the shape of a sandglass.

The back portion B and the stomach portion C of the diaper 1 each include a waist portion D in which a waist extensible potion 12 is provided as illustrated in FIG. 3.

As illustrated in FIG. 3, the back portion B includes a below-waist portion E, and the laterally extensible portion 7 is provided on both side areas of the below-waist portion E. Each laterally extensible portion 7 is a composite member formed by joining two rectangular sheets having a plurality of elastic threads 71 interposed therebetween in a parallel alignment in their stretched state. Nonwoven fabric is preferably used as the sheets.

A fastening tape 13 is attached along the laterally outer edge of each laterally extensible panel 7 so that the fastening tapes 13 stick out laterally.

The pair of laterally extensible portions 7 are fixed between the cover sheet 11 and the exterior sheet 8 as illustrated in FIG. 4 with the elastic threads 71 being laterally stretched out. As illustrated in FIG. 3, the pair of laterally extensible portions 7 are provided at least in the region outboard of the side edges 41 of the absorbent member 4 and are absent in the widthwise middle region of the absorbent member 4. Such arrangement includes (1) the configuration of FIG. 4, in which each laterally extensible portion 7 overlaps the region of the absorbent member 4 inboard of the side edge 41, and (2) a configuration (not shown) in which each laterally extensible portion 7 is immediately outboard of the side edge of the absorbent member 4 with no overlap between the extensible portion 7 and the absorbent member 4. Either way, it is desirable that the absorbent member 4 disposed in the widthwise middle portion of the diaper not be gathered.

The pair of the elasticized standing cuffs 6 of the diaper 1 according to the first embodiment are each formed of a cuff-forming sheet 62 having elastic members 61. The sheet 62 is placed to straddle the inboard side and the outboard side of each side edge of the topsheet 2 as illustrated in FIG. 2.

As illustrated in FIG. 3, each cuff 6 has two elastic threads as the elastic members 61 disposed substantially parallel to the free edge 64 of the cuff 6.

The pair of cuffs 6 are each fixed to the back portion B at one longitudinal end thereof and to the stomach portion C at the other end.

The cuffs 6 rise almost upright with respect to the topsheet 2 in the crotch portion A in their relaxed state as illustrated in FIG. 2. The cuff 6 is fixed to the back portion B at one of its longitudinal ends (rear end) such that the portion inboard of the fixed end 63 is fixed to the topsheet 2 as illustrated in FIG. 4. The cuff 6 is fixed to the stomach portion C at the other end (front end) in the same manner.

According to the first embodiment, since the leak-preventive sheet 3 extends into the inside of the leg flaps 5 (see FIG. 2), the diaper 1 provides enhanced side leak protection.

Since the side edge of the leak-preventive sheet 3 in the leg flap 5 in the crotch portion A is inboard of the most outboard elastic member 51A, the sheet 62 shaping the free edge part of the leg flap 5 is easily gathered to form a frill. This provides improved tightness between the leg flaps 5 and wearer's legs.

When the disposable diaper 1 of the first embodiment in a folded packaged condition is unfolded, the pair of leg flaps 5 in their relaxed state spread laterally outward except for the vicinities of the fixed portions 52 and 53 so that they are successfully prevented from being tucked inside when put on a wearer.

Disposable diapers 1 according to the second to fourth embodiments will then be described with reference to FIGS. 5 through 10. Unless otherwise described, the description about the first embodiment appropriately applies to the second to fourth embodiments. The members and regions in FIGS. 5 to 10 identical to those in FIGS. 1 to 4 are given the same numerals as in FIGS. 1 to 4.

Figure 5:
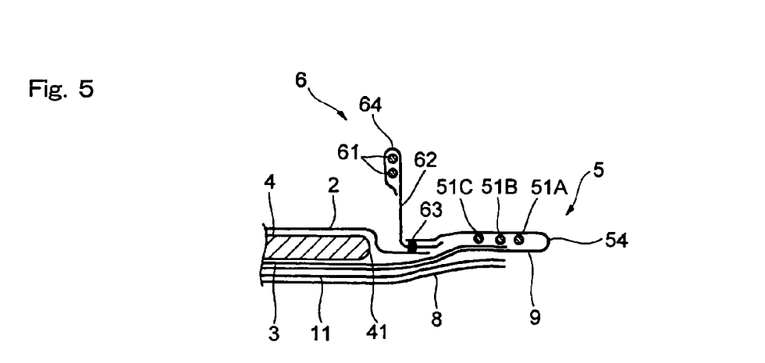
FIG. 5 is an enlarged cross-section corresponding to FIG. 2, schematically illustrating a diaper according to a second embodiment of the invention in its relaxed state.

In the disposable diaper 1 of the second embodiment, each of the leg flaps 5 is formed of an auxiliary sheet 9 as illustrated in FIG. 5. The auxiliary sheet 9 underlies the leak-preventive sheet 3, extends laterally outward from the side edges 41 of the absorbent member, folds back over its upper side while embracing the leak-preventive sheet 3 and the elastic members 51A, 51B and 51C, and joins with the cuff-forming sheet 62 along the fixed end 63.

Figure 6:
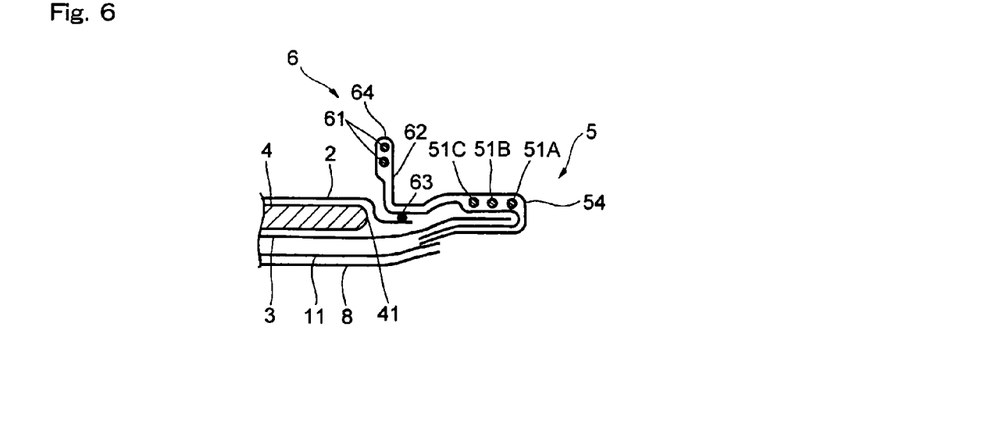
FIG. 6 is an enlarged cross-section corresponding to FIG. 2, schematically illustrating a diaper according to a third embodiment of the invention in its relaxed state.

In the disposable diaper 1 of the third embodiment, the cuff 6 and the leg flap 5 on each side of the diaper 1 are integrally formed of a single sheet 62. As illustrated in FIG. 6, the inboard one of the two facing panels of the sheet 62 having the elastic members 61 sandwiched therebetween extends laterally outward, covers the elastic members 51A, 51B and 51C of the leg flap 5, overlaps with the other panel of the sheet 62 to form the cuff 6 and the leg flap 5 integrally. Both side portions of the sheet 62 joining with each other fold back downward to form the free edge 54 of the leg flap 5.

The leak-preventive sheet 3 in the diaper 1 of the third embodiment is inserted in the fold of the thus folded-back sheet 62 and bonded thereto.

According to the third embodiment, the outer side of the leg flap 5 is formed of the leak-preventive sheet 3 and three thicknesses of the sheet 62 in a superposed relation to provide enhanced leakage protection.

Figure 7:
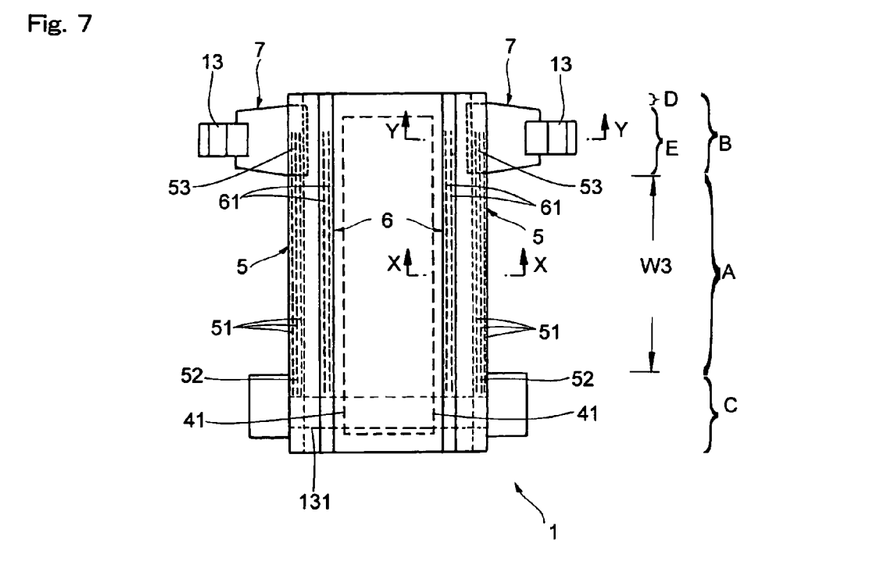
FIG. 7 is a plan of a diaper according to a fourth embodiment of the invention in its flat-pit state.

In the fourth embodiment, a pair of elastic panels 7 are provided on the laterally opposing side portions of the below-waist portion E of the back portion B as the pair of laterally extensible portions 7 of the first embodiment as illustrated in FIG. 7.

Each of the elastic panels 7 is a composite member composed of a trapezoidal resin film extensible lengthwise and crosswise and a nonwoven fabric of the same shape as the resin film superposed on both sides of the resin film. The elastic panel 7 is extensible in every part thereof in both the diaper's longitudinal and lateral directions. A pair of fastening tapes 13 are attached to the laterally outer side of the elastic panels 7 as illustrated in FIG. 7.

Figure 9:
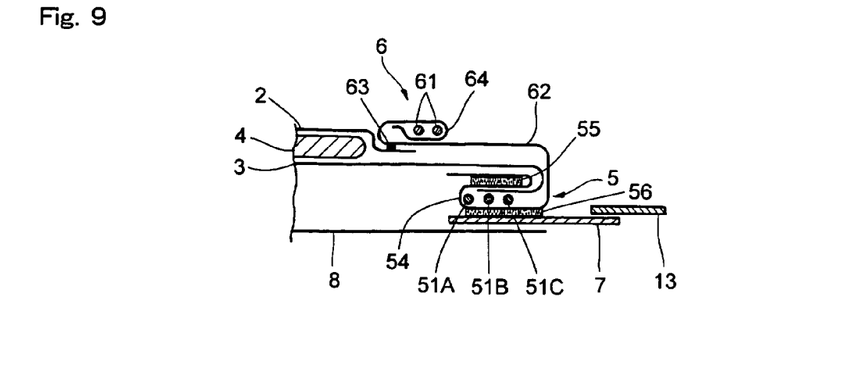
FIG. 9 is an enlarged cross-section schematically illustrating the fourth embodiment of FIG. 7, taken along line IV-IV.

In the fourth embodiment, the rear end portion of each leg flap 5 is joined in the fixed portion 53 to the upper side of the elastic panel 7, which is joined to the upper side of the exterior sheet 8 as illustrated in FIG. 9. The front end portion of the leg flap 5 is joined in the fixed portion 52, where the elastic panel 7 is absent, directly to the upper side of the exterior sheet 8.

Figure 8:
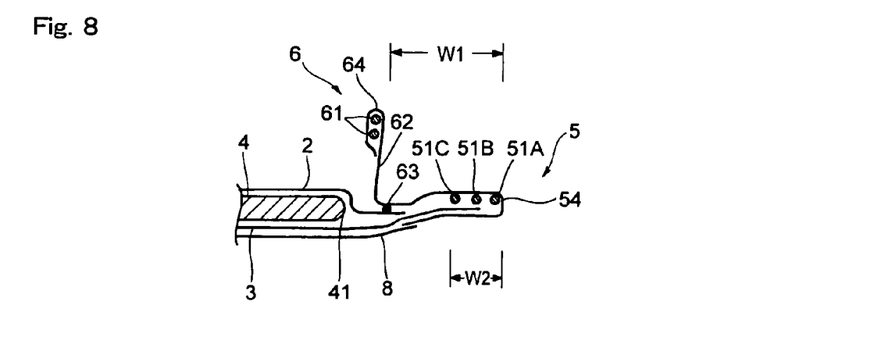
FIG. 8 is an enlarged cross-section corresponding to FIG. 2, schematically illustrating the diaper of the fourth embodiment illustrated in FIG. 7 in its relaxed state, taken along line III-III.

The most outboard elastic member 51A of the leg flap 5 is disposed along or near the laterally outer edge of the leg flap 5 as illustrated in FIG. 8. Therefore, there is no or substantially no frill formed of the sheet 62 outboard of the elastic member 51A.

The diaper 1 of the fourth embodiment is provided with a pair of elasticized, standing cuffs 6 along the laterally opposing sides of the absorbent member 4. Each cuff 6 is fixed at the front and rear end portions thereof in a configuration such that the cuff 6 may fall or fold laterally outward as illustrated in FIG. 9 when the disposable diaper 1 is in a flat-out state with the elastic members 61 of the cuffs 6 and the elastic members 51A, 51B, and 51C of the leg flaps 5 stretched out.

In more detail, the rear end portion of each cuff 6 is folded over the sheet 62 about the fixed end 63 and fixed thereto as illustrated in FIG. 9 to provide a rear fixed portion 53. Similarly, the front end portion of the cuff 6 is also folded and fixed to provide a front fixed portion 52.

When the disposable diaper 1 is in its relaxed state, the cuff 6 stands from the topsheet 2 with the free edge 64 inclining outwardly in the crotch portion A, as illustrated in FIG. 8.

The cover sheet 11 is not provided in the fourth embodiment.

Figure 10A:
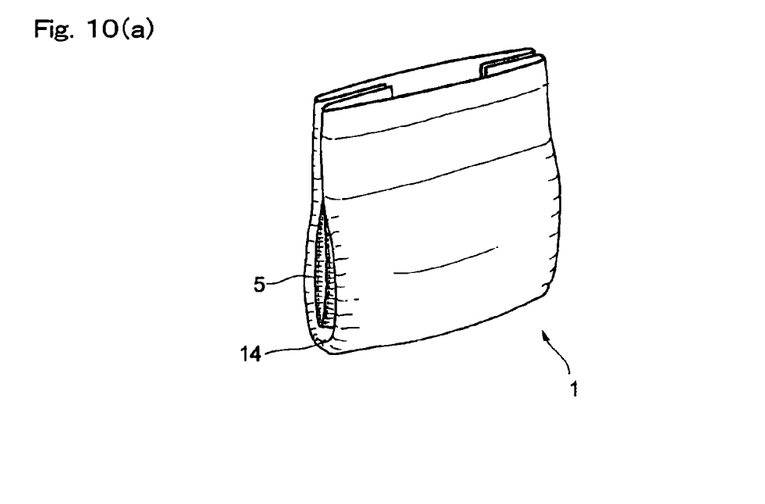
FIG. 10(a) is a perspective of the diaper of the fourth embodiment in its folded state.

In packaging for sale, the disposable diaper 1 of the fourth embodiment is pre-folded as follows. Each of the opposing leg flaps 5 is fixed at its front and rear end portions in a configuration such that the whole length of the laterally distal portion of the leg flap 5 where the elastic members 51A, 51B, and 51C are provided may be folded back over the side of the leak-preventive sheet 3 when the diaper is in a flat-out state. In this state, each of the laterally opposite side portions of the diaper 1 is folded lengthwise over the skin facing side along a position between the elastic member 51A of the leg flap 5 and the side edge 41 of the absorbent member 4 as illustrated in FIG. 10(a). The diaper 1 with its both side portions so folded in is further folded in two about its lateral centerline with the skin facing side inside. As a result, a folded edge or bend 14 is formed along near the lateral centerline of the diaper 1.

Figure 10B:
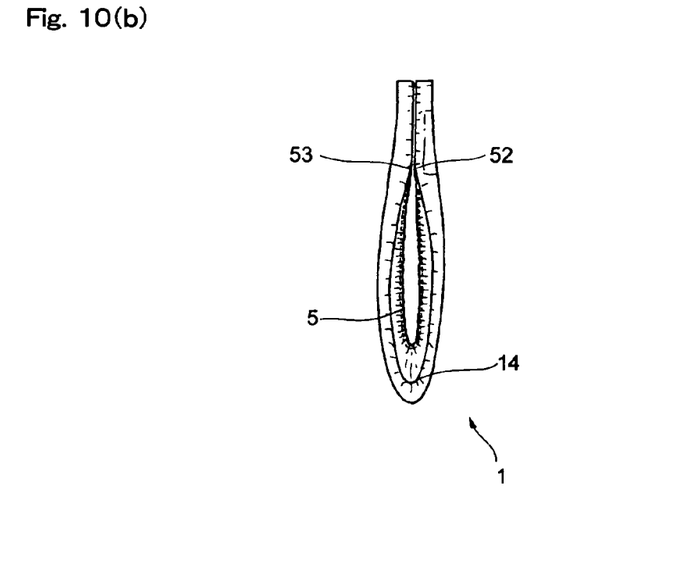
FIG. 10(b) is a side view of the diaper of the fourth embodiment in its folded state.

In the thus folded and relaxed state, each leg flap 5 is close to the garment facing side of the diaper 1 near the fixed portions 52 and 53 in the front and the rear end portions while it is less close to the garment facing side near the folded bend 14 as illustrated in FIG. 10(b). While FIG. 10(b) shows only one side view of the folded diaper 1, the other side has the same view.

In greater detail, each leg flap 5 is joined to the garment facing side of the diaper in the fixed portions 52 and 53 but gradually separates from the garment facing side of the diaper toward the bend 14. The part of each leg flap 5 outboard of the most inboard elastic member 51C sticks laterally outward and extends almost horizontally near the bend 14 as illustrated in FIGS. 10(a) and 10(b).

The disposable diapers 1 each pre-folded in the above described manner are packaged in a single pack for sale as follows.

A package of the present invention includes an outer casing containing a plurality of the disposable diapers 1. In packaging, the plurality of the disposable diapers 1 are stacked one on top of another with all the edges aligned in the thickness direction thereof.

Preferably, two stacks of the disposable diapers thus formed are placed side-by-side and wrapped in a casing made of a resin film.

In the fourth embodiment, the width W1 of the leg flap 5 is preferably constant over the whole length of the leg flap 5 as measured between the fixed end 63 and the free edge 54 in a direction perpendicular to the longitudinal direction along the surface of the leg flap 5 in its flat-out state. Specifically, the width W1 is preferably 10 to 70 mm, more preferably 20 to 50 mm.

The width W2 between the inboard edge of the elastic member 51C and the free edge 54 measured in a direction perpendicular to the longitudinal direction along the surface of the leg flap 5 in its flat-out state is preferably constant over the whole length of the leg flap 5. Specifically, the width W2 is preferably 5 to 50 mm, more preferably 10 to 35 mm.

The length W3 of the leg flap 5 in the crotch portion A in its flat-out state is preferably 50 to 400 mm, more preferably 100 to 300 mm.

According to the fourth embodiment, since the elastic panels 7 used in place of the laterally extensible portions of the first embodiment do not contract in the lateral direction, the folded-back portions are not gathered in their end portions, being prevented from becoming uselessly thicker and harder to cause discomfort to a wearer. Being extensible all over, the elastic panels 7 extend seemingly obliquely when pulled. As a result, the diaper 1 provides an improved fit about the wearer's crotch to buttocks, particularly near the fixed portions of the folded-back portions.

The sheet 62 forms no or substantially no frills along the laterally distal edge of the leg flaps 5 so that there is no possibility of a frill being tucked into the inside of the leg openings when the diaper is put on a child.

Since the standing cuffs 6 are fixed at their front and rear end portions in a configuration such that they are folded over laterally outward when the diaper is in a flat-out state, they stand while worn with laterally outward inclination to provide enhanced leakage protection.

When the disposable diaper 1 of the fourth embodiment in the above-described folded condition is unfolded, the pair of leg flaps 5 in their relaxed state spread or open laterally outward so that they are successfully prevented from being tucked inside when put on a wearer.

The process of producing a disposable diaper according to the present invention will now be described with respect to preferred embodiments of the process for producing the above described diapers.

A first preferred embodiment of the process of producing the disposable diaper according to the invention is carried out, for example, as follows.

The process of the first embodiment starts with the preparation of a continuous body of the absorbent body. The continuous body of the absorbent body includes a continuous body of the topsheet, a continuous body of the backsheet, a plurality of absorbent members 4 disposed between the continuous body of the topsheet and the continuous body of the backsheet, and a pair of continuous body of the leg flaps having an elastic member 51. The pair of continuous body of the leg flaps are disposed along the opposite edges of the plurality of absorbent members 4. Each of the continuous body of the leg flaps is folded back over the side of the continuous body of the backsheet along a position inboard of the elastic member 51, and the folded-back portion of each of the continuous body of the leg flaps is joined to the continuous body of the backsheet at predetermined intervals. Separately, a continuous body of the exterior sheet is prepared by cutting a continuous sheet of fiber to make concave shapes along opposite edges at a prescribed interval symmetrically about the longitudinal centerline. The continuous body of the absorbent body is then joined to the continuous body of the exterior sheet in alignment such that each pair of leg flaps 5 of the continuous body of the absorbent body may stick out laterally from the edge of the concave shapes of the continuous body of the exterior sheet. The continuous body of the exterior sheet is cut between adjacent individual absorbent bodies 16 into individual disposable diapers. In this embodiment, the continuous body of the backsheet is a continuous body of the leak-preventive sheet.

In the present embodiment, the absorbent body is prepared in what we call a longitudinal transfer system in which the longitudinal direction of the absorbent body is parallel with the machine direction.

In more detail, absorbent members 4 are placed at equal spacing on a continuous body of the leak-preventive sheet that is a leak-preventive fiber sheet of continuous length. A continuous body of the topsheet that is a liquid permeable fiber sheet of continuous length is superposed thereon, and the two bodies are fusion bonded together between the adjacent absorbent members 4. The spacing between the adjacent absorbent members 4 corresponds to the total length of regions which will become a back portion B and a stomach portion C, respectively, after separated into individual disposable diapers and are contiguously connected to each other on their waist edges, measured in the longitudinal direction in the flat-out state.

A separately prepared pair of continuous body of the leg flaps are then joined along the opposite side edges of the plurality of absorbent members 4 with the elastic members 51 stretched out to prepare a continuous body of the absorbent body. It is preferred that a continuous body of the cuff be simultaneously formed of the continuous leak-preventive sheet of fiber that forms each continuous body of the leg flap. In this case, both side portions of each continuous sheet of fiber are folded back and bonded to itself while wrapping an elastic thread (elastic member 61) for elasticizing the continuous body of the cuff inside the fold on one side and the elastic thread (elastic member 51) for elasticizing the continuous body of the leg flap inside the other fold on the other side. Thus, a continuous body of the leg flap and a continuous body of the cuff are simultaneously provided along each side of the continuous body of the absorbent body.

The continuous body of the leg flap provided along each side of the continuous body of the absorbent body is then folded back over the side of the continuous body of the backsheet about a folding line inboard of the elastic member 51. The folded-back portion of the continuous body of the leg flap is fixed to the continuous body of the backsheet at predetermined intervals. The regions to be fixed will be the front and rear end portions of each leg flap 5 in finally obtained individual disposable diapers.

Separately, a pair of laterally extensible portions 7 are formed on laterally opposing side portions of a continuous body of the exterior sheet, which is a separately provided continuous length fiber sheet, at a predetermined interval in the longitudinal direction. Each of the laterally extensible portions 7 is formed by bonding a plurality of elastic members 71 of thread form to the continuous body of the exterior sheet in their stretched state in parallel with the lateral direction. A pair of fastening tapes 13 are attached to the outboard edge of each laterally extensible portion 7 to stick out laterally.

A continuous body of the cover sheet that is another fiber sheet of continuous form is superposed on the continuous body of the exterior sheet, and the two continuous bodies are joined with the elastic members 71 of the laterally extensible portions 7 stretched in the lateral direction to make a continuous exterior laminate sheet. The two continuous bodies are preferably joined over the entire area.

The resulting continuous exterior laminate sheet is cut along opposite side edges to make a concave contour at a predetermined interval in a symmetrical configuration about the longitudinal centerline of the laminate sheet. Every cut is made between the laterally extensible portions 7 arranged at a prescribed interval in the longitudinal direction. The thus cut continuous exterior laminate sheet has a symmetrical shape about its longitudinal centerline with its width reduced from both sides at a prescribed interval. The portions having a reduced width will provide leg openings when individual disposable diapers are worn. The cutting is preferably carried out by means of a rotary cutting tool, water jetting, punching, and the like.

Each region of the continuous exterior laminate sheet between the adjacent concave shapes in the longitudinal direction corresponds to the regions which will become a back portion B and a stomach portion C, respectively, after separated into individual disposable diapers and are contiguously connected to each other on their boundaries which will become waist edges. Accordingly, it is preferred that the pair of laterally extensible portions 7 be formed on both side portions of the regions that will each become the back portion B of the individual disposable diapers.

The continuous body of the absorbent body is then joined to the continuous exterior laminate sheet in alignment such that each pair of leg flaps 5 of the continuous body of the absorbent body may stick out laterally from the edge of the laterally opposing concave shapes of the continuous body of the exterior sheet. In the present embodiment, each absorbent body 16 is bonded to the continuous body of the exterior sheet via the continuous body of the cover sheet.

The continuous body of the absorbent body and the continuous exterior laminate sheet are cut between adjacent individual absorbent bodies 16 into individual disposable diapers of the present invention.

In spacedly placing the absorbent members 4 on the continuous body of the leak-preventive sheet, the length of the individual absorbent members should be shorter than the length of the disposable diaper so that the cutting positions of the continuous web assembly may not be across the individual absorbent members.

According to the first embodiment of the process, disposable diapers incorporating the above-described embodiment are produced.

The process of producing a disposable diaper according to the present invention also includes the following second preferred embodiment. Unless otherwise described hereunder, the description of the first embodiment of the process applies to the second embodiment.

In the second embodiment of the process of producing the disposable diaper according to the present invention, a laterally extensible portion 7 is formed on both side portions of a continuous body of the exterior sheet, which is a separately provided fiber sheet of continuous length, at a predetermined interval in the longitudinal direction. The laterally extensible portion 7 is formed by bonding a plurality of elastic members 71 of thread form to the continuous body of the exterior sheet in their stretched state in parallel with the lateral direction. A pair of fastening tapes 13 are attached to the outboard edge of each laterally extensible portion 7 to stick out laterally. The pair of laterally extensible portions 7 are preferably formed on both side portions of regions that will be the back portion B of the individual disposable diapers.

A continuous body of the cover sheet, which is another fiber sheet of continuous form, is superposed on the continuous body of the exterior sheet, and the two continuous bodies are joined with the elastic members 71 of the laterally extensible portions 7 stretched in the lateral direction to make a continuous laminate sheet. The two continuous bodies are preferably joined over the entire area.

The resulting continuous laminate sheet is cut at a prescribed interval into a plurality of continuous exterior laminate sheets. The cutting interval corresponds to a total length of regions which will become a back portion B and a stomach portion C, respectively, after separated into individual disposable diapers and are contiguously connected to each other on their boundaries which will become waist edges, measured in the longitudinal direction in the flat-out state. The cutting position is between a region that will become a back portion B and a region that will become a stomach portion C. The continuous exterior laminate sheet used in the present embodiment lacks a region that will become a crotch portion A of a diaper. The continuous exterior laminate sheet is a couple of regions which will become a back portion B and a stomach portion C, respectively, of a disposable diaper and are contiguously connected to each other on their boundaries which will become waist edges.

Each of the resulting continuous exterior laminate sheets is joined to the garment facing side of the continuous body of the absorbent body in a position as to straddle two adjacent individual absorbent bodies 16 arrayed in the continuous body of the absorbent body. The region of the continuous exterior laminate sheet that is provided with a pair of laterally extensible portions 7 is joined to one of the two adjacent absorbent bodies 16, while the other region that is not provided with a pair of laterally extensible portions 7 is joined to the other absorbent body 16. The continuous exterior laminate sheet may be joined to the moving continuous body of the absorbent body with its region having the pair of laterally extensible portions 7 either forward or rearward relative to the machine direction.

In that manner, a plurality of continuous exterior laminate sheets are successively joined to the garment facing side of the continuous body of the absorbent body.

Finally, each continuous exterior laminate sheet is cut across between the adjacent individual absorbent bodies 16 into individual disposable diapers according to the present invention.

According to the second embodiment, the disposable diaper of the aforementioned embodiment can be produced. In this embodiment, since the exterior sheet 8 and the cover sheet 11 are absent in the crotch portion A, the cost of producing the diapers can be reduced.

The process of producing a disposable diaper according to the present invention also includes the following third preferred embodiment. Unless otherwise described, the description about the first embodiment appropriately applies to the third embodiment.

The process of the third embodiment starts with the preparation of a continuous body of the absorbent body. The continuous body of the absorbent body includes a continuous body of the topsheet, a continuous body of the backsheet, a plurality of absorbent members 4 disposed between the two continuous bodies, and a pair of continuous body of the leg flaps each having an elastic member 51. The pair of continuous body of the leg flaps are disposed along the opposing side edges of the plurality of absorbent members 4. Each of the continuous body of the leg flaps is folded back over the side of the continuous body of the backsheet along a position inboard of the elastic member 51, and the folded-back portion of each of the continuous body of the leg flaps is joined to the continuous body of the backsheet at predetermined intervals. The continuous body of the absorbent body is then cut across between every adjacent absorbent members 4 into individual absorbent bodies 16. Thereafter, the absorbent bodies 16 are joined to a separately prepared continuous body of the exterior sheet at a predetermined interval, and the continuous body of the exterior sheet is cut between adjacent absorbent bodies 16 into individual disposable diapers.

According to the third embodiment, the disposable diapers of the aforementioned embodiment can be obtained.

The disposable diaper of the present invention is not limited to the foregoing embodiments, and various modifications can be made thereto without departing from the spirit and scope of the invention as exemplified as follows.

The pair of leg flaps 5 in the first embodiment of the disposable diaper 1 may be replaced with the pair of leg flaps 5 used in the fourth embodiment. The pair of leg flaps 5 used in the fourth embodiment may be replaced with that used in the second or third embodiment.

The bag-shaped portion of the sheet 62 in which the elastic member of the leg flap 5 is embraced does not need to be formed of a single sheet. For example, the bag-shaped portion may be formed of a laterally outward extension of the backsheet 3 combined with the sheet 62 while sandwiching the elastic member therebetween. The topsheet 2 and the backsheet 3 may both extend laterally outward to embrace the elastic member.

When the disposable diaper of the invention has a pair of laterally extensible portions 7 on both side portions of the below-waist portion D of the back portion B, and the absorbent member 4 is preferably disposed symmetrically about the transverse centerline of the diaper, it is possible to apply the back portion B to the stomach side of a wearer. Thus, the diaper is easy to put even on a wearer lying on its stomach or standing facing or not facing a caregiver as well as a wearer lying on its back.

In each of the above embodiments of the disposable diaper, the laterally extensible portion may be replaced with an elastic panel. Being a monolithic unitary member, the elastic panel merely has to be connected directly to the continuous body of the exterior sheet or the continuous exterior laminate sheet without requiring the use of the continuous body of the cover sheet. The other details are the same as described above.

The disposable diaper of the invention is for use by not only children but adults.

In the description given above, particulars of a certain embodiment that have been omitted to avoid redundancy can appropriately be complemented by the corresponding description of other embodiments. Particulars described as being characteristic of a certain embodiment can apply to other embodiments as appropriate. Particulars of every embodiment are appropriately interchangeable between embodiments.

INDUSTRIAL APPLICABILITY

According to the present invention, the leg flaps spread or open laterally outward in the crotch portion in a relaxed state of the diaper. Therefore, the leg flaps are prevented from being tucked into the inner side of the diaper whereby leak protection is provided. The diaper needs no check and untucking operation around the leg openings by a caregiver. This helps every diaper change go smoothly.

The invention claimed is:

1. A process of producing a disposable diaper comprising a topsheet, a backsheet, an absorbent member between the topsheet and the backsheet, and a pair of leg flaps along laterally opposing side edges of the absorbent member, the leg flaps being elasticized with an elastic member, said method comprising the steps of:
    making a continuous body of the absorbent body comprising a continuous body of the topsheet, a continuous body of the backsheet, a plurality of absorbent members disposed between the topsheet and the backsheet, and a pair of continuous body of the leg flaps having an elastic member, the pair of continuous body of the leg flaps being disposed along the opposing side edges of the plurality of absorbent members,
    folding back each of the continuous body of the leg flaps over the continuous body of the backsheet side along a position inboard of the elastic member,
    joining the folded-back portion of each of the continuous body of the leg flaps to the continuous body of the backsheet at predetermined intervals,
    separately preparing a continuous body of the exterior sheet by cutting a continuous sheet of fiber to make concave shapes on both edges at a prescribed interval symmetrically about the longitudinal centerline,
    joining the continuous body of the absorbent body to the continuous body of the exterior sheet in alignment such that each pair of leg flaps of the continuous body of the absorbent body may stick out laterally from the edge of the concave shapes of the continuous body of the exterior sheet, and
    cutting the continuous body of the exterior sheet between individual absorbent bodies into individual disposable diapers,
    wherein each leg flap is fixed at a front and a rear end portion thereof to longitudinally opposite end portions of the diaper, respectively, in such a configuration that the leg flap may be folded back over the backsheet side when the disposable diaper is in a flat-out state with the elastic members stretched.

2. A process of producing a disposable diaper comprising a topsheet, a backsheet, an absorbent member between the topsheet and the backsheet, and a pair of leg flaps along laterally opposing side edges of the absorbent member, the leg flaps being elasticized with an elastic member, said method comprising the steps of:
    making a continuous body of the absorbent body comprising a continuous body of the topsheet, a continuous body of the backsheet, a plurality of absorbent members disposed between the topsheet and the backsheet, and a pair of continuous body of the leg flaps having an elastic member, the pair of continuous body of the leg flaps being disposed along the opposing side edges of the plurality of absorbent members,
    folding back each of the continuous body of the leg flaps over the continuous body of the backsheet side along a position inboard of the elastic member,
    joining the folded-back portion of each of the continuous body of the leg flaps to the continuous body of the backsheet at predetermined intervals,
    separately preparing a plurality of continuous body of the exterior sheets by cutting a continuous sheet of fiber at a predetermined interval,
    joining each of the continuous body of the exterior sheets to the continuous body of the absorbent body to straddle two adjacent individual absorbent bodies, and
    cutting each continuous body of the exterior sheet between the adjacent individual absorbent bodies into individual disposable diapers,
    wherein each leg flap is fixed at a front and a rear end portion thereof to longitudinally opposite end portions of the diaper, respectively, in such a configuration that the leg flap may be folded back over the backsheet side when the disposable diaper is in a flat-out state with the elastic members stretched.

3. The process of producing a disposable diaper according to claim 1 or 2, wherein the disposable diaper further comprises an exterior sheet on the outer side of the backsheet, wherein the fixed front and rear end portions of each leg flap are covered with the exterior sheet.

4. The process of producing a disposable diaper according to claim 1 or 2, wherein the elastic member of each leg flap is disposed along or near the laterally outer edge of the leg flap, and there is no or substantially no frill outboard of the elastic member.

5. The process of producing a disposable diaper according to claims 1 or 2, wherein the disposable diaper further comprises a pair of elasticized standing cuffs each having an elastic member, each of the cuffs being fixed at a front and a rear end portion thereof in a configuration such that the cuff may fold laterally outward when the diaper is in a flat-out state with all the elastic members of the cuffs and of the leg flaps being stretched.

6. The process of producing a disposable diaper according to claim 1 or 2, wherein one of the longitudinally opposite end portions of the diaper has a laterally extensible portion on both lateral side portions thereof, one of the front and the rear end portions of each leg flap being fixed in an overlapping or a crossing relation with the laterally extensible portion.

7. The process of producing a disposable diaper according to claim 1 or 2, wherein the disposable diaper further comprises a pair of fastening tapes on one of the longitudinally opposite end portions and having, on the other end portion, a landing zone where the fastening tapes are adapted to be secured.

8. The process of producing a disposable diaper according to claim 1 or 2, wherein each of laterally opposite side portions of the diaper is folded lengthwise over the skin facing side along a position between the elastic member of the leg flap and the side edge of the absorbent member, the diaper with its both side portions so folded is further folded in two about its lateral centerline with the skin facing side inside, and each leg flap is close to the garment facing side near the fixed front and rear end portions thereof while it is less close to the garment facing side near the lateral centerline of the diaper.

9. The process of producing a disposable diaper according to claim 1 or 2, wherein the leg flap is folded back over the backsheet side when the disposable diaper is in a flat-out state with the elastic members stretched.

10. The process of producing a disposable diaper according to claim 1 or 2, wherein each leg flap is fixed to the diaper in a configuration such that an entire length of a laterally distal portion of each leg flap where elastic members are provided, is folded back over a side of the backsheet.

* * * * *